United States Patent [19]
Sander et al.

[11] Patent Number: 5,530,587
[45] Date of Patent: Jun. 25, 1996

[54] STEREOMICROSCOPE WITH ADJUSTABLE OBJECTIVE AND PRISMATIC CUBES

[75] Inventors: Ulrich Sander, Oberkochen; Ulrich Lemcke, Heidenheim, both of Germany

[73] Assignee: Carl-Zeiss-Stiftung, Heidenheim, Germany

[21] Appl. No.: 390,761

[22] Filed: Feb. 17, 1995

[30] Foreign Application Priority Data

Feb. 17, 1994 [DE] Germany .......................... 44 04 987.0

[51] Int. Cl.⁶ .................................................. G02B 21/22
[52] U.S. Cl. .......................................... 359/376; 359/377
[58] Field of Search ................................... 359/368, 407, 359/411, 413, 471, 472, 473, 373–384

[56] References Cited

U.S. PATENT DOCUMENTS 5,321,447 6/1994 Sander et al. ........................ 351/216

FOREIGN PATENT DOCUMENTS 9003458 7/1990 Germany .
9305447 8/1993 Germany .

*Primary Examiner*—Timothy P. Callahan
*Assistant Examiner*—Jeffrey Zweizig
*Attorney, Agent, or Firm*—Walter Ottesen

[57] ABSTRACT

The invention is directed to a stereomicroscope having a main objective of variable focal intercept. An optical element is provided in each of the two stereoscopic component beam paths to provide a parallel displacement of the particular beam path. A coupling between each displacement of the two stereoscopic beam paths and the actual adjustment of the focal intercept of the main objective is also provided in such a manner that a preselectable constant stereo angle results even when there is a variation of the focal intercept of the main objective. In this way, a physiologically constant viewing impression results for the viewer.

13 Claims, 2 Drawing Sheets

STEREOMICROSCOPE WITH ADJUSTABLE OBJECTIVE AND PRISMATIC CUBES

FIELD OF THE INVENTION

The invention relates to a stereomiscroscope having a main objective of variable focal intercept. The stereomicroscope ensures that the physiological viewing impression remains constant even for a variation of the focal intercept of the main objective.

BACKGROUND OF THE INVENTION

Published German utility model registration G 9,003, 458.9 discloses a main objective of variable focal intercept for surgical microscopes. This main objective essentially comprises two optical units which can be displaced relative to each other. The focal intercept of the main objective on the object side can be varied in dependence upon the relative displacement. However, for a variation of the focal intercept of this kind, there results, inter alia, also a variation of the stereo angle.

With increasing requirements imposed upon the optical power capacity of surgical microscopes, a varying stereo angle, which occurs in dependence upon the adjusted focal intercept of the main objective and therefore a varying physiological viewing impression, is disadvantageous for the surgeon.

SUMMARY OF THE INVENTION

In view of the foregoing, it is an object of the invention to provide a stereomicroscope which avoids the above-mentioned disadvantages of the state of the art. It is also an object of the invention to provide a physiological viewing impression in the stereomicroscope which remains constant even when the focal intercept of the main objective on the object side is varied.

The stereomicroscope of the invention defines a pair of stereoscopic viewing beam paths along which corresponding viewing beams travel from an object to an observer. The stereomicroscope includes: a main objective for directing the beam paths toward the object at a preselected stereo angle ($\delta_S$); the main objective having an object side facing toward the object and defining a focal intercept at the object side; first adjusting means for acting on the main objective to vary and adjust the focal intercept; first and second optical elements mounted in respective ones of the beam paths downstream of the main objective as seen in the direction from the object toward the observer; second adjusting means for acting on the optical elements for laterally displacing the viewing beam paths relative to each other; and, coupling means for coupling said first and second adjusting means to each other for holding the preselected stereo angle ($\delta_S$) constant for the observer when actuating the first adjusting means to adjust the focal intercept.

According to a feature of the invention, a coupling is provided between the adjustment of the focal intercept of the main objective and the parallel displacement of the stereoscopic component beam paths downstream of the main objective. This feature ensures that a constant stereo angle is always provided for the viewer even when there is a variation of the focal intercept of the main objective at the object side.

A series of possibilities exists for the coupling of the invention in dependence upon the desired precision and complexity.

A further deterioration of the desired constant physiological viewing impression results with a main objective of variable focal intercept in addition to the stereo angle dependent upon the focal intercept. This deterioration results because the magnification of the total optical system of the stereomicroscope is, inter alia, also dependent upon the particular focal intercept of the main objective on the object side. When varying this focal intercept, the total magnification of the stereomicroscope thereby does not remain constant; instead, this total magnification varies within specific limits. According to the invention, the detected object-side focal intercept of the main objective is therefore not only applied to maintain the stereo angle constant but also functions as an input variable to maintain the total magnification of the stereomicroscope constant in a stereomicroscope having a magnification change device. Accordingly, the inherent magnification of the magnification change device is controlled in dependence upon the focal intercept via a further second coupling. The magnification change device is arranged downstream of the main objective having the variable focal intercept.

Overall, a constant physiological viewing impression results in the stereomicroscope for the viewer independently of the adjusted object-side focal intercept of the main objective. A series of advantages results thereby especially for utilization of the stereomicroscope of the invention as a surgical microscope.

The couplings according to the invention are advantageously engaged and disengaged selectively via appropriate operator-actuated elements so that the viewer can select between different operating modes of the stereomicroscope of the invention.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
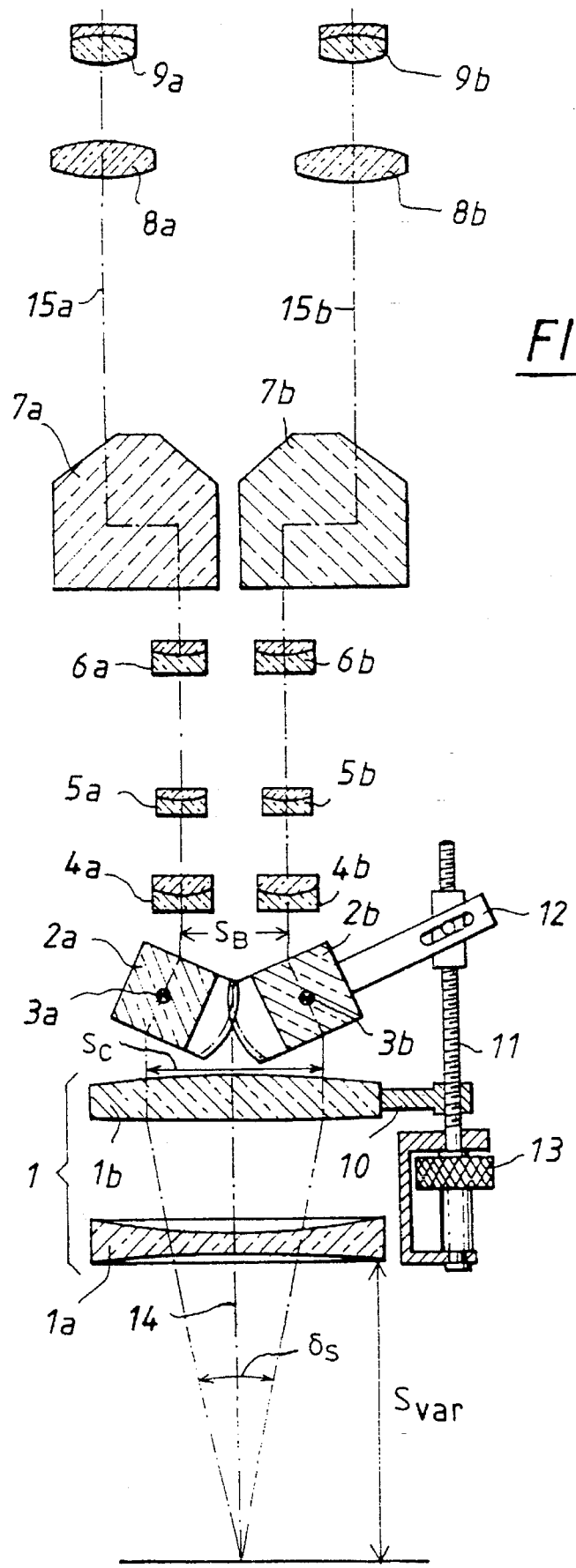
FIG. 1 is a schematic of a first embodiment of the stereomicroscope according to the invention; and, FIG. 2 is a second embodiment of the stereomicroscope of the invention wherein, additionally, a coupling is provided between the main objective focal intercept and the magnification change device.

A first embodiment of the stereomicroscope according to the invention is shown schematically in FIG. 1. The stereomicroscope of the invention includes a main objective 1 having an object-side variable focal intercept $S_{var}$. The main objective 1 comprises two separate lenses (1a, 1b). The negative lens 1a is arranged at the front end of the main objective and is fixedly mounted in the housing of the stereomicroscope. The positive lens 1b is displaceable along the optical axis 14 in a defined manner. The main objective 1 of variable focal intercept corresponds to the main objective shown in German utility model registration G 9,003, 458.9 and, with the aid of this main objective 1, a variation of the focal width on the object side is possible in a range of 150 mm to 450 mm.

Optical elements (2a, 2b) are mounted in corresponding ones of stereoscopic component beam paths on the viewing side of the main objective. The stereoscopic component beam paths can be laterally displaced in a defined manner with the optical elements (2a, 2b) in the region between the main objective 1 and the downstream magnification change device (4a, 5a, 6a; 4b, 5b, 6b). It is here noted that the embodiment of the stereoscopic microscope of the invention does not necessarily require the magnification change device (104a, 105a, 106a; 104b, 105b, 106b).

The two optical elements (2a, 2b) are configured as mutually synchronized prismatic cubes which are each rotatable about an axis (3a or 3b). These axes (3a, 3b) are perpendicular to the optical axes (15a, 15b) of the stereoscopic component beams. Each of the prismatic cubes engages via a toothed wheel in the toothed wheel mounted on the other axis (3a or 3b) so that, when one prismatic cube is tilted, a corresponding synchronous tilt of the other prismatic cube in the other stereoscopic component beam path occurs in the opposite direction by the same angular amount. The optical axes (15a, 15b) of the two stereoscopic beam paths are then each displaced by the same amount parallelly inwardly or outwardly.

A mechanical embodiment of an arrangement of this kind is disclosed in U.S. patent application Ser. No. 08/223,333, filed Apr. 5, 1994, which is incorporated herein by reference. With the aid of this arrangement, a defined selective adjustment of the stereobasis is realized but no coupling to the focal intercept of the main objective is provided.

Optical elements of a known magnification change device (4a, 5a, 6a; 4b, 5b, 6b) are mounted in the stereoscopic component beam paths downstream of the two rotatable optical elements (2a, 2b). The magnification desired by the operator can be definitively adjusted by a corresponding displacement of one or more optical elements of the magnification change device (4a, 5a, 6a; 4b, 5b, 6b). In lieu of the continuous magnification change device shown, a known Galilei changer having discrete magnification steps can be utilized as a magnification change device. Furthermore, in a simple embodiment of the stereomicroscope of the invention, it is possible to omit the magnification change device (104a, 105a, 106a; 104b, 105b, 106b).

The magnification change device (4a, 5a, 6a; 4b, 5b, 6b) is followed in the stereoscopic beam paths on the viewing side by the image-erecting prisms (7a, 7b) as well as the tubular and ocular lenses (8a, 9a; 8b, 9b) which are arranged in a manner known per se.

Furthermore, the stereomicroscope includes an illuminating device (not shown) having at least one light source as well as one or more deflecting elements.

According to the invention, a constant stereo angle $\delta_S$ is provided for the viewer by means of a coupling between the object-side focal intercept adjustment of the main objective 1 and the tilting of the prismatic cubes. The stereo angle $\delta_S$ is maintained constant in accordance with the invention and can furthermore be preselected by means of the two prismatic cubes.

In advance of surgery, the operating surgeon adjusts the desired stereo angle $\delta_S$ via an operator-actuated element (not shown) in dependence upon the requirement. The once adjusted stereo angle $\delta_S$ is maintained constant by maintaining constant the spacing $S_c$ of the two optical axes (15a, 15b) of the stereoscopic component beam paths by means of a corresponding tilt movement of the two prismatic cubes in dependence upon the focal intercept of the main objective 1. This is done even though this spacing $S_c$ varies directly behind the main objective 1 and therefore the stereo angle $\delta_S$ actually also varies in dependence upon the focal intercept of the main objective. In this way, and because of the coupling of the invention, a constant stereo angle $\delta_S$ is always provided for the viewer independently of the particular focal intercept of the main objective.

Depending upon whether the focal intercept variation of the spacing $S_c$ becomes larger or smaller, the resulting change $\delta S_c$ of this spacing must be compensated by a corresponding mutually opposing tilt movement of the two prismatic cubes so that the optical axes (15a, 15b) of the two stereoscopic component beam paths always exhibit the same constant spacing $S_c$.

In the embodiment of FIG. 1, a mechanical coupling between the focal intercept adjustment of the main objective 1 and the parallel displacement of the optical axes (15a, 15b) of the two stereoscopic beam paths is provided in order to ensure the constant stereo angle $\delta_S$ for the viewer. For this purpose, the displaceable lens 1b of the main objective 1 of variable focal intercept is connected via a connecting element 10 to a spindle drive 11. The spindle drive 11 couples the movement of this lens 1b along the optical axis 14 to the tilt movement of the downstream optical elements (2a, 2b) about the respective pivot axes (3a, 3b) in the stereoscopic component beam paths. At least one of the two optical elements (2b) is likewise connected to the spindle drive 11 via a further connecting element 12. It is here desired to obtain a coupling which provides a constant stereo angle $\delta_S$ independently of the particular focal intercept of the main objective 1. Accordingly, the tilt movement of the prismatic cubes must be matched to the linear displacement of the movable lens 1b of the main objective 1. If required, a suitable displacement cam has to be dimensioned on the connecting element 12 between the prismatic cube and the spindle drive 11.

The adjustment of the focal intercept $S_{var}$ of the main objective takes place manually in the illustrated embodiment via an actuating element 13. This actuating element 13 is connected to the spindle drive 11 or to the displaceable lens 1b. Alternatively, a motorized displacement of the lens 1b and a corresponding motorized displacement of the two prismatic cubes via suitable drives is possible at any time.

The mechanical coupling shown in FIG. 1 between the focal intercept of the main objective and the stereo angle $\delta_S$ can be realized constructively in a different manner. What is essential for the invention is, that in each case, a coupling is provided in such a manner that the stereo angle $\delta_S$ is constant also when there is a variation of the focal intercept of the main objective at the object side thereof.

Figure 2:
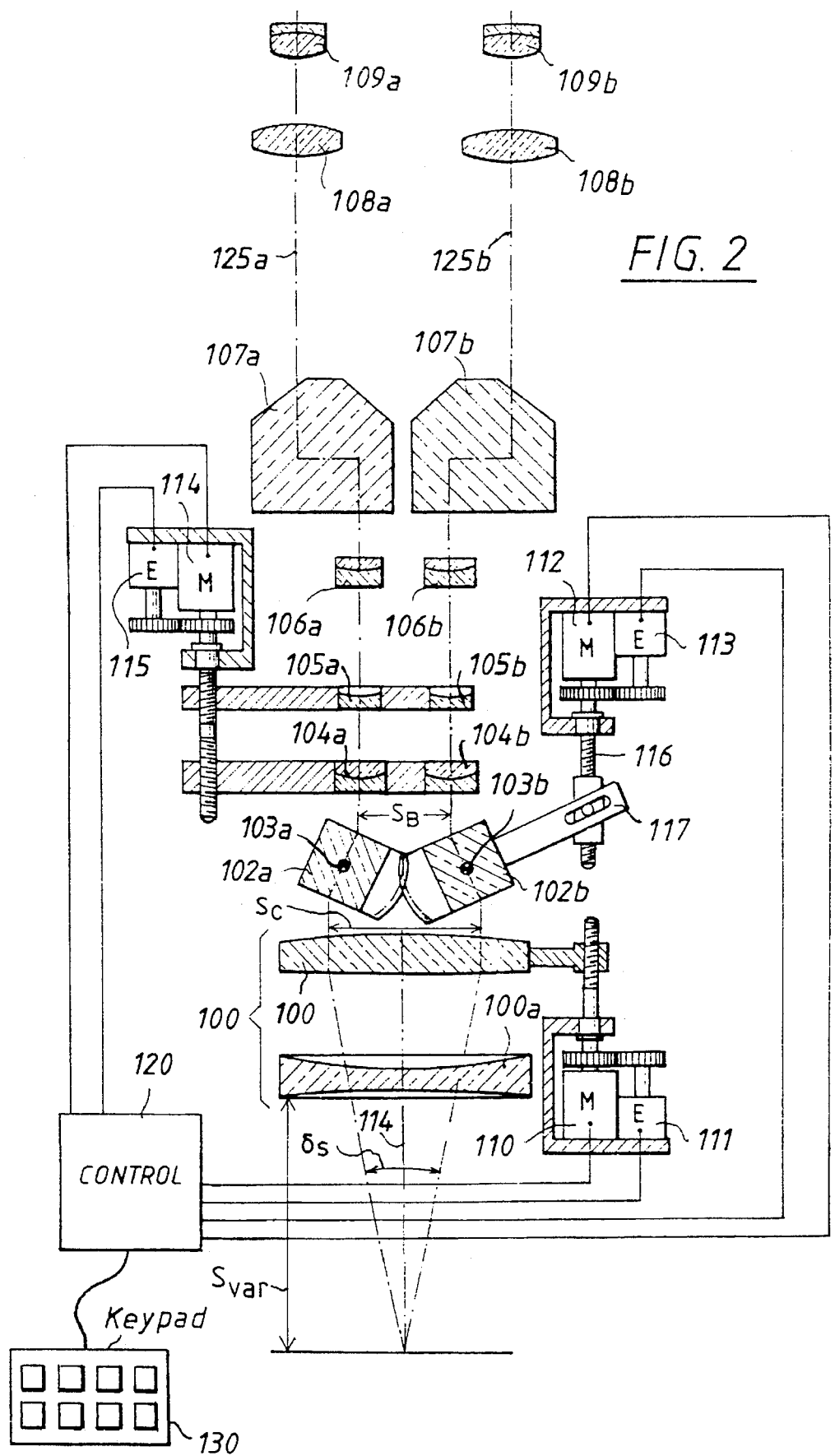

A further embodiment of the stereomicroscope of the invention is shown schematically in FIG. 2.

The optical system of this embodiment of the stereomicroscope of the invention corresponds essentially to the optical system of the embodiment of FIG. 1. Accordingly, the optical system of the stereomicroscope of FIG. 2 likewise includes a main objective 100 of variable focal intercept $S_{var}$. This main objective comprises a fixedly positioned negative lens 100a and a positive lens 100b which is movable relative to lens 100a. The two optical elements (102a, 102b) are configured as prismatic cubes and are downstream of the main objective 100. The elements (102a, 102b) are synchronously pivoted about respective axes (103a, 103b) in mutually opposite directions. These axes (103a, 103b) are perpendicular to the optical axes (125a, 125b) of the two stereoscopic component beam paths. A magnification change device (104a, 105a, 106a; 104b, 105b, 106b) follows the elements (102a, 102b) and makes possible a continuous variation of the adjusted magnification. For this purpose, a known pancratic magnification change device is provided. Furthermore, correcting prisms (107a, 107b) as well as tubular and ocular lenses (108a, 109a; 108b, 109b) are provided in the stereoscopic component beam paths as known per se.

The embodiment of the stereomicroscope of FIG. 2 is distinguished from that shown in FIG. 1 in that the displacement of the movable lens 100b of the main objective 100 now takes place via a motorized drive 110. The particular position of the movable lens 100b on the optical axis 114 is detected via a corresponding encoder 111. The particular adjusted focal intercept of the main objective is then always known. The control of the motorized drive 110 as well as the evaluation of the position data supplied by the encoder 111 are performed by a central servo control 120.

The required tilt movement of the two optical elements (102a, 102b) takes place via a further motorized drive 112 in correspondence to the evaluated encoder data for the particular position of the movable lens 100b on the optical axis 114 (that is, the actual adjusted object side focal intercept of the main objective 100) to maintain the stereo angle $\delta_S$ constant. The elements (102a, 102b) are configured as prismatic cubes.

Tilting, in turn, takes place via a spindle drive 116 and a lever rod 117 coupled thereto. The lever rod 117 connects the motor drive 112 to one of the two optical elements 103b. The actual angle position of the two optical elements (102a, 102b) and the parallel displacement of the optical axes (125a, 125b) of the stereoscopic beam paths is detected in the embodiment shown with the aid of an encoder 113.

A servo controlled coupling between the focal intercept adjustment of the main objective 100 and the displacement of the stereoscopic component beam paths by the central servo control 120 ensures that a constant stereo angle $\delta_S$ for the viewer is provided when the spacing $S_c$ between the optical axes (125a, 125b) of the stereoscopic component beam paths varies directly rearward of the main objective 100.

Depending upon the desired complexity, the servo controlled coupling can either be configured as an open-loop control circuit or a closed-loop control circuit. The servo control 120 continuously detects also the actual tilt position of the two prismatic cubes and the resulting parallel displacement in the closed-loop control circuit embodiment shown in FIG. 2. However, on the other hand, a feed-back of this kind can be omitted in the open-loop control circuit variation. An embodiment of this kind of the servo control coupling is correspondingly less expensive with respect to control complexity.

In the embodiment of FIG. 2, the detected data with respect to the actual focal intercept of the main objective 100 are now no longer used simply for coupling with the angular position of the two optical elements (102a, 102b) and holding the stereo angle $\delta_S$ constant but furthermore are used as input variables to adjust a constant total magnification of the optical system of the stereomicroscope according to the invention.

For this purpose, one or several of the optical elements of the magnification change device (104a, 105a, 106a; 104b, 105b, 106b) are likewise connected to a motorized drive 114. This drive 114 provides a corresponding displacement along the optical axes and therewith a defined adjustment of the magnification. An encoder 115 is assigned to drive 114 and continuously detects the particular magnification of the magnification change device (104a, 105a, 106a; 104b, 105b, 106b). All encoder data are detected and correspondingly evaluated, in turn, by the central servo control 120.

In this embodiment of the stereomicroscope of the invention, a second coupling is realized which, in turn, controls (open loop or closed loop) one other variable of the stereomicroscope relative to viewing, namely, the adjustment of the total magnification. This control is performed in dependence upon the actual focal intercept of the main objective 100 on the object side thereof. A constant total magnification of the optical system of the stereomicroscope is sought via a corresponding open-loop or closed-loop control circuit. The desired total magnification of the stereomicroscope of the invention can be selected by the operator via a keypad 130 mounted, for example, on the stereomicroscope.

With this keypad, the operator can selectively switch in or switch out the first coupling between the focal intercept adjustment of the main objective 100 and the displacement of the stereoscopic component beam path and the second coupling between the focal intercept of the main objective and the total magnification of the optical system of the stereomicroscope. Also, a desired total magnification of the pancratic system can be adjusted with the aid of the keypad. The total magnification selected in each case is, as above, held constant during the course of the surgery.

The coupling described last between the particular focal intercept of the main objective and the total magnification of the optical system of the stereomicroscope can also be utilized independently of the above-described first coupling to realize a constant stereo angle in the stereomicroscope. It is only necessary to detect the focal intercept of the main objective and to provide the coupling to the total magnification.

In addition to the servo controlled coupling shown in FIG. 2, this coupling can also be realized via a mechanical variation such as via a cam drive or the like.

Furthermore, it has been shown advantageous when all the above-described couplings can be engaged and disengaged selectively by the operator via suitable operator-actuated elements so that a series of possible modes of operation are provided for the stereomicroscope of the invention.

It is understood that the foregoing description is that of the preferred embodiments of the invention and that various changes and modifications may be made thereto without departing from the spirit and scope of the invention as defined in the appended claims.

What is claimed is:

1. A stereomicroscope defining a pair of stereoscopic viewing beam paths along which corresponding viewing beams travel from an object to an observer, the stereomicroscope comprising:

a main objective for directing said beam paths toward the object at a preselected stereo angle ($\delta_S$);

said main objective having an object side facing toward the object and defining a focal intercept at said object side;

first adjusting means for acting on said main objective to vary and adjust said focal intercept;

first and second optical elements mounted in respective ones of said beam paths downstream of said main objective as seen in the direction from the object toward the observer;

second adjusting means for acting on said optical elements for laterally displacing said viewing beam paths relative to each other; and, coupling means for coupling said first and second adjusting means to each other for holding said preselected stereo angle ($\delta_S$) constant for the observer when actuating said first adjusting means to adjust said focal intercept.

2. The stereomicroscope of claim 1, said first and second optical elements being first and second prismatic cubes pivotally mounted on respective first and second pivot axes; and, said pivot axes being perpendicular to corresponding ones of said beam paths.

3. The stereomicroscope of claim 2, said second adjusting means interconnecting said prismatic cubes for synchronously rotating said cubes in mutually opposite directions toward each other.

4. The stereomicroscope of claim 1, wherein said coupling means is a mechanical coupling interconnecting said first and second adjusting means.

5. The stereomicroscope of claim 4, said second adjusting means comprising: a first arcuate segment having a first set of gear teeth formed thereon; a second arcuate segment having a second set of gear teeth formed thereon; said first and second arcuate segments being mounted on corresponding ones of said first and second optical elements so as to cause said first and second sets of teeth to intermesh.

6. The stereomicroscope of claim 1, said coupling means being a servo controlled coupling of said first and second adjusting means.

7. The stereomicroscope of claim 1, said coupling means being a first coupling means; and, said stereomicroscope further comprising: a magnification change device arranged in said viewing beam paths downstream of said first and second optical elements; and, second coupling means for coupling said first adjusting means to said magnification change device for providing a constant total magnification of said stereomicroscope selected by the observer which is independent of the adjustment of said focal intercept.

8. The stereomicroscope of claim 7, said second coupling means being a mechanical coupling.

9. The stereomicroscope of claim 7, said second coupling means being a servo controlled coupling of said first adjusting means and said magnification change device.

10. The stereomicroscope of claim 7, further comprising: control means for controlling said first and second coupling means; and, keypad means connected to said control means for allowing an operator to selectively switch each of said first and second coupling means on and off.

11. The stereomicroscope of claim 10, said keypad means being mounted on the stereomicroscope and being adapted for operating on said magnification change device to provide a defined adjustment of the total magnification of said stereomicroscope.

12. A method for operating a stereomicroscope defining a pair of stereoscopic viewing beam paths along which corresponding viewing beams travel from an object to an observer, the stereomicroscope including: a main objective for directing said beam paths toward the object at a preselected stereo angle ($\delta_S$); and, the main objective having an object side facing toward the object and defining a variable focal intercept at the object side, the method comprising the steps of:

continuously detecting said focal intercept; and, compensating a lateral displacement of said beam paths caused by a variation of said focal intercept so as to always cause said preselected stereo angle ($\delta_S$) to be constant for the viewer.

13. The method of claim 12, further comprising the steps of:

providing said stereomicroscope with a magnification change device; and, holding the magnification of said stereomicroscope constant in dependence upon said focal intercept.

* * * * *